(12) United States Patent
Klosin et al.

(10) Patent No.: US 6,646,071 B1
(45) Date of Patent: Nov. 11, 2003

(54) METAL COMPLEXES CONTAINING BRIDGING HETEROATOM FOR OLEFIN-POLYMERIZATION-PROCESS

(75) Inventors: Jerzy Klosin, Midland, MI (US); Peter N. Nickias, Sanford, MI (US)

(73) Assignee: The Dow Chemical Company, Midland, MI (US)

( * ) Notice: Subject to any disclaimer, the term of this patent is extended or adjusted under 35 U.S.C. 154(b) by 0 days.

(21) Appl. No.: 09/936,120

(22) PCT Filed: Mar. 17, 2000

(86) PCT No.: PCT/US00/07371

§ 371 (c)(1),
(2), (4) Date: Sep. 6, 2001

(87) PCT Pub. No.: WO00/69870

PCT Pub. Date: Nov. 23, 2000

Related U.S. Application Data

(60) Provisional application No. 60/133,995, filed on May 13, 1999.

(51) Int. Cl.⁷ ............................. C08F 4/64; C08F 4/642
(52) U.S. Cl. ................. 526/127; 526/126; 526/161; 526/172; 526/943; 502/103; 502/152; 502/155; 556/11; 556/52
(58) Field of Search ................. 502/155, 152, 502/103; 526/161, 172, 943, 126, 127; 556/52, 11

(56) References Cited

U.S. PATENT DOCUMENTS

| 5,055,438 A | 10/1991 | Canich |
|---|---|---|
| 5,057,475 A | 10/1991 | Canich et al. |
| 5,064,802 A | 11/1991 | Stevens et al. |
| 5,096,867 A * | 3/1992 | Canich .................. 502/103 |
| 5,132,380 A | 7/1992 | Stevens et al. |
| 5,304,614 A | 4/1994 | Winter et al. |
| 5,321,106 A | 6/1994 | LaPointe |
| 5,350,817 A | 9/1994 | Winter et al. |
| 5,374,696 A | 12/1994 | Rosen et al. |
| 5,470,993 A | 11/1995 | Devore et al. |
| 5,621,126 A | 4/1997 | Canich et al. |
| 5,703,187 A | 12/1997 | Timmers |
| 5,721,185 A | 2/1998 | LaPointe et al. |

FOREIGN PATENT DOCUMENTS

| EP | 416815 | 3/1991 |
|---|---|---|
| EP | 514828 | 11/1992 |
| EP | 577581 | 1/1994 |
| EP | 852230 | 7/1998 |
| JP | 9-124722 | * 5/1997 |
| JP | 11199621 | 7/1999 |
| WO | WO 95/07942 | 3/1995 |
| WO | WO 96/13529 | 5/1996 |
| WO | WO 98/06727 | 2/1998 |
| WO | WO 98/06728 | 2/1998 |

OTHER PUBLICATIONS

Plenio et al., J. Organometallic Chem. 519 (1996) 269–272.*
E. Barsties, S. Schaible, M. H. Prosenc, U. Rief, W. Roll, O. Weyland, B. Dorerer, and H. H. Brintzinger.
J. Organometallic Chem. 1996, 519, 269–272, H. Plenio, and D. Birth Chemical Abstracts vol. 13, No. 11, Abstract #. 144972q, Iwase, K, "Preparation of Ethylen–Stryene Copolymer and Its Polymerization Catalysts Containing Group IVB Metal Complexes" (XP 002139516), 1999.
Journal of Chemical Society. Vol 88, No. 3, 1996 pp. 446–452. Dahl, L. F. et al, Preparation and Structures of Methyl Phenylpropilate–Iron Carbonyl Complexes. A New DICARBON7YL–PI–Cyclopentadienyloxy–Sigma—VI Nyliron Compound.
JACS 88:3 (1996) 446–452.

* cited by examiner

*Primary Examiner*—David W. Wu
*Assistant Examiner*—R. Rabago

(57) ABSTRACT

Metal complexes comprising an oxygen, sulfur, or nitrogen containing bridging group which are useful as catalyst components for the polymerization of olefins.

20 Claims, 1 Drawing Sheet

METAL COMPLEXES CONTAINING BRIDGING HETEROATOM FOR OLEFIN-POLYMERIZATION-PROCESS

This application claims the benefit of No. 60/133,995 filed May 13, 1999.

FIELD OF THE INVENTION

This invention relates to a class of metal complexes, the ligands used to prepare these metal complexes and to olefin polymerization catalysts derived therefrom that are particularly suitable for use in a polymerization process for preparing polymers by polymerization of α-olefins and mixtures of α-olefins.

BACKGROUND

Constrained geometry metal complexes and methods for their preparation are disclosed in U.S. Pat. No. 5,703,187; U.S. Pat. No. 5,321,106; U.S. Pat. No. 5,721,185; U.S. Pat. No. 5,374,696; U.S. Pat. No. 5,055,438; U.S. Pat. No. 5,057,475; U.S. Pat. No. 5,096,867; U.S. Pat. No. 5,064,802; U.S. Pat. No. 5,132,380; U.S. Pat. No. 5,470,993, as well as EP-A-514,828, and elsewhere.

U.S. Pat. No. 5,350,817 and U.S. Pat. No. 5,304,614 disclose bridged zirconocene complexes, wherein two indenyl groups are covalently linked together by a bridge containing carbon or silicon, which are useful for the polymerization of propylene.

EP-A-577,581 discloses unsymmetrical bis-Cp metallocenes containing a fluorenyl ligand with heteroatom substituents.

E. Barsties; S. Schaible; M.-H. Prosenc; U. Rief; W. Roll; O. Weyland; B. Dorerer; H.-H. Brintzinger *J. Organometallic Chem.* 1996, 520, 63–68, and H. Plenio; D. Birth *J. Organometallic Chem.* 1996, 519, 269–272 disclose systems in which the cyclopentadienyl ring of the indenyl is substituted with a dimethylamino group in non-bridged and Si-bridged bis-indenyl complexes useful for the formation of isotactic polypropylene and polyethylene.

Disclosure of random heteroatom substitution in mono-Cp metallocenes is found in EP-A-416,815, WO 95/07942, WO 96/13529, and U.S. Pat. No. 5,096,867 and U.S. Pat. No. 5,621,126. Specific heteroatom substitution of the 3- and 2-position of indenyl complexes of group 4 metals was disclosed in WO 98/06727 and WO/98/06728 respectively. The foregoing specifically substituted metal complexes have produced improved catalyst results, however, problems still remain with catalyst efficiency and deactivation of the catalyst under high temperature polymerization conditions. It would be advantageous to be able to produce polyolefins with higher molecular weights. It would also be advantageous to be able to improve other physical characteristics of the polymers produced by altering the substitution around the cyclopentadienyl group of the metallocene complexes used in olefin polymerization catalyst systems.

SUMMARY OF THE INVENTION

Figure 1:
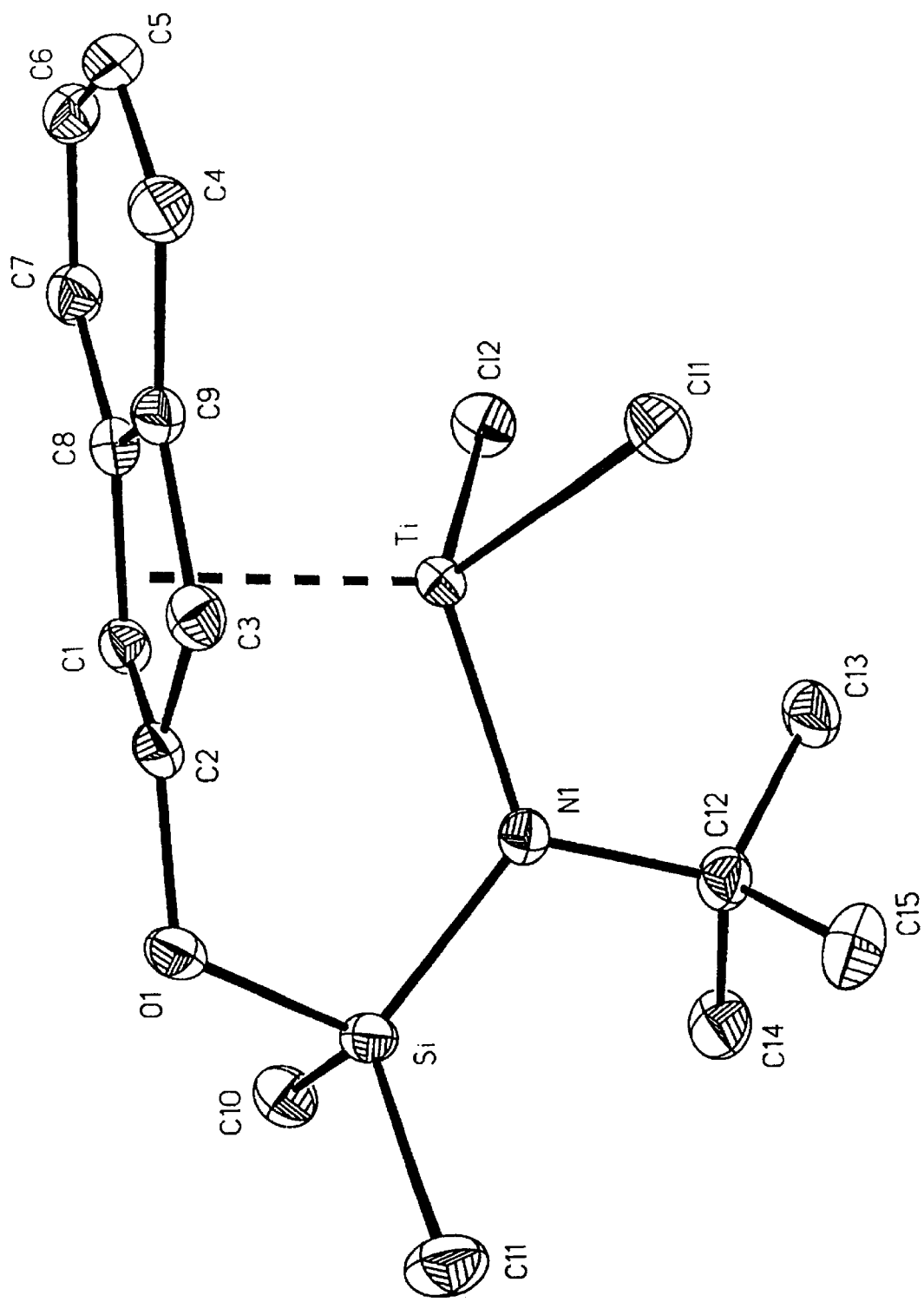
FIG. 1 is an ORTEP drawing based on X-ray analysis of the compound prepared in Example 3.

According to the present invention there are provided metal complexes corresponding to the formula:

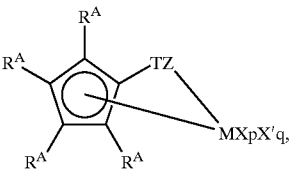

where M is a metal from one of Groups 3 to 13 of the Periodic Table of the Elements, the lanthanides or actinides, which is in the +2, +3 or +4 formal oxidation state;

T is oxygen, sulfur, or NR, wherein R is alkyl or cycloalkyl of up to 10 carbons;

$R^A$ independently each occurrence is hydrogen, $R^B$ or $T^B{}_j$, j is 1 or 2, and when j is 1, T' is oxygen or sulfur and when j is 2, T' is nitrogen or phosphorus, $R^B$ independently each occurrence is a group having from 1 to 80 atoms not counting hydrogen, which is hydrocarbyl, hydrocarbylsilyl, halo-substituted hydrocarbyl, hydrocarbyloxy-substituted hydrocarbyl, hydrocarbylamino-substituted hydrocarbyl, or hydrocarbylsilyl-substituted hydrocarbyl, or two $R^B$ groups are joined together forming a divalent ligand group;

Z is a divalent moiety bound to T and bound to M by either covalent or coordinate/covalent bonds, comprising boron or a member of Group 14 of the Periodic Table of the Elements, and also comprising nitrogen, phosphorus, sulfur or oxygen;

X is an anionic or dianionic ligand group having up to 60 atoms (including ligands that are cyclic, delocalized, π-bound ligand groups);

X' independently each occurrence is a Lewis base ligand having up to 20 atoms;

p is a number from 0 to 5, (when each X is an anionic ligand, p is two less than the formal oxidation state of M, when some or all X groups are dianionic ligand groups each dianionic X group accounts for two valencies and p is correspondingly reduced in value); and q is zero, 1 or 2.

Certain of the metal complexes wherein the metal is a Group 3 or lanthanide metal are catalytically active for polymerization of olefins without addition of an activator or cocatalyst. Preferably however a cocatalyst is present. Accordingly, in one embodiment according to the present invention, there is provided a catalyst composition for olefin polymerization comprising:

(A) a catalyst component comprising a metal complex as previously defined; and (B) a cocatalyst component comprising an activating cocatalyst wherein the molar ratio of (A) to (B) is from 1:10,000 to 100:1; or optionally catalyst component (A) is activated by use of an activating technique.

Another embodiment of this invention is a catalyst composition for olefin polymerization comprising:

(A) a catalyst component comprising a metal complex as previously defined; and (B) a cocatalyst component comprising an activating cocatalyst wherein the molar ratio of (A) to (B) is from 1:10,000 to 100:1 wherein the metal complex is in the form of a radical cation.

Further according to the present invention there is provided a process for the polymerization of olefins comprising contacting one or more $C_{2-20}$ α-olefins under polymerization conditions with one of the aforementioned catalyst compositions.

A preferred process of this invention is a high temperature solution polymerization process for the polymerization of olefins comprising contacting one or more $C_{2-20}$ α-olefins under polymerization conditions with one of the aforementioned catalyst compositions at a temperature from 100° C. to 250° C.

Within the scope of this invention are the polyolefin products produced by the aforementioned processes. Preferred products have long chain branching and/or reverse molecular architecture.

This invention also provides a cyclopentadienyl-containing ligand of one of the aforementioned metal complexes where the ligand is in the form of:

(A) a free acid with 2 protons capable of being deprotonated;

(B) a dilithium, disodium or dipotassium salt;

(C) a magnesium salt: or (D) a mono or disilylated dianion.

Within the scope of this aspect of the invention is the use of one of these ligands for synthesis to produce a metal complex of this invention, or, more specifically, the use of one of these ligands for synthesis to produce a metal complex comprising a metal from one of Groups 3 to 13 of the Periodic Table of the Elements, the lanthanides or actinides, and from 1 to 4 of the ligands.

The present catalysts and processes result in the highly efficient production of high molecular weight olefin polymers over a wide range of polymerization conditions, and especially at elevated temperatures. They are especially useful for the solution or bulk polymerization of ethylene/propylene (EP polymers), ethylene/octene (EO polymers), ethylene/styrene (ES polymers), propylene, and ethylene/propylene/diene (EPDM polymers) wherein the diene is ethylidenenorbornene, 1,4-hexadiene or similar nonconjugated diene. The use of elevated temperatures dramatically increases the productivity of such processes due to the fact that increased polymer solubility at elevated temperatures allows the use of increased conversions (higher concentration of polymer product) without exceeding solution viscosity limitations of the polymerization equipment. In addition, the use of higher polymerization temperatures results in a reduction of energy costs needed to devolatilize the reaction product.

The catalysts of this invention may also be supported on a support material and used in olefin polymerization processes in a slurry or in the gas phase. The catalyst may be prepolymerized with one or more olefin monomers in situ in a polymerization reactor or in a separate process with intermediate recovery of the prepolymerized catalyst prior to the primary polymerization process.

DETAILED DESCRIPTION

All references to the Periodic Table of the Elements herein shall refer to the Periodic Table of the Elements, published and copyrighted by CRC Press, Inc., 1989. Also, any reference to a Group or Groups shall be to the Group or Groups as reflected in this Periodic Table of the Elements using the IUPAC system for numbering groups. The full teachings of any patent, patent application, provisional application, or publication referred to herein are hereby incorporated by reference. The term "reverse molecular architecture" as used herein refers to a copolymer of two or more olefins wherein higher molecular weight fractions of the polymer contain increased content of the higher molecular weight comonomer.

Olefins as used herein are $C_{2-20}$ aliphatic or aromatic compounds containing vinylic unsaturation, as well as cyclic compounds such as cyclobutene, cyclopentene, and norbornene, including norbornene substituted in the 5- and 6-positions with $C_{1-20}$ hydrocarbyl groups. Also included are mixtures of such olefins as well as mixtures of such olefins with $C_{4-40}$ diolefin compounds. Examples of the latter compounds include ethylidene norbornene, 1,4-hexadiene, norbornadiene, and the like. The catalysts and processes herein are especially suited for use in preparation of ethylene/1-butene, ethylene/1-hexene, ethylene/styrene, ethylene/propylene, ethylene/1-pentene, ethylene/4-methyl-1-pentene and ethylene/1-octene copolymers as well as terpolymers of ethylene, propylene and a nonconjugated diene, such as, for example, EPDM terpolymers.

Preferred coordination complexes according to the present invention are complexes corresponding to the formulas:

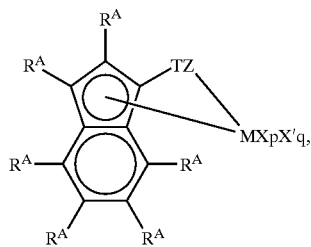

II where T, T', $R^A$, $R^B$, j, Z, X, X', and q are as previously defined,

M is a Group 4 metal, preferably Ti; and p is 0, 1 or 2.

Preferably $R^A$ independently is hydrogen, $R^B$ or $T'R^B_j$, where $R^B$ is a group having from 1 to 20 atoms not counting hydrogen, which is hydrocarbyl, hydrocarbylsilyl, halo-substituted hydrocarbyl, or hydrocarbylsilyl-substituted hydrocarbyl, or two $R^A$ groups are joined together forming a divalent ligand group.

Preferably T is O and T' is O or N, more preferably N.

Preferred $T'R^B_j$ groups are at the 3, 5, or 6-position of the substituted indenyl group and or those wherein the $T'R^B_j$ group is methoxy, ethoxy, propoxy, methylethylo 1,1-dimethyethyloxy, trimethylsiloxy, 1,1-dimethylethyl (dimethylsilyl)oxy, dimethylamino, diethylamino, methylethylamino, methylphenylamino, dipropylamino, dibutylamino, piperidino, morpholino, pyrrolidino, hexahydro-1H-azepin-1-yl, hexahydro-1(2H)-azocinyl, octahydro-1H-azonin-1-yl or octahydro-1(2H)-azecinyl, or two adjacent $T'R^B_j$ groups are —$OCH_2O$—. More preferred are those wherein the $T'R^B_j$ group is dimethylamino, methylphenylamino, piperidino or pyrrolidino.

Preferred X groups are halide, alkyl, cycloalkyl, aryl, aralkyl or cycloalkadienyl groups, said X having from 1 to 20 atoms other than hydrogen.

Preferred X' groups are carbon monoxide; phosphines, especially trimethylphosphine, triethylphosphine, triphenylphosphine and bis(1,2-dimethylphosphino)ethane; $P(OR^C)_3$, wherein $R^c$ is hydrocarbyl, silyl or a combination thereof; ethers, especially tetrahydrofuran; amines, especially pyridine, bipyridine, tetramethylethylenediamine (TMEDA), and triethylamine; olefins; and conjugated dienes having from 4 to 40 carbon atoms. Complexes including the latter X' groups include those wherein the metal is in the +2 formal oxidation state.

More preferred $R^A$ groups are hydrogen, alkyl, aryl, aralkyl, alkoxy, dihydrocarbylamino, and hydrocarbyleneamino, said $R^A$ group having from 1 to 20 nonhydrogen atoms, most preferably hydrogen, alkyl, aryl, N,N-dimethylamino and pyrrolidino.

Highly preferred complexes include ones corresponding to the formula:

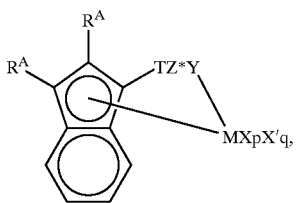

III where, T, $R^A$, M, X, X', p and q are as previously defined with respect to formula I, Y is —O—, —S—, —NR*—, —NR*$_2$, or —PR*—;

Z* is SiR*$_2$, CR*$_2$, SiR*$_2$SiR*$_2$, CR*$_2$CR*$_2$, CR*=CR*, CR$_2$SiR*$_2$, CR*$_2$SiR*$_2$CR*$_2$, SiR*$_2$CR*$_2$SiR*$_2$, CR*$_2$CR*$_2$SiR*$_2$, CR*$_2$CR*$_2$CR*$_2$, or GeR*$_2$; and R* independently each occurrence is hydrogen, or a member selected from hydrocarbyl, hydrocarbyloxy, silyl, halogenated alkyl, halogenated aryl, and combinations thereof, said R* having up to 20 nonhydrogen atoms, and optionally, two R* groups from Z, or an R* group from Z and an R* group from Y form a ring system.

Most highly preferred are the metal complexes corresponding to the formula:

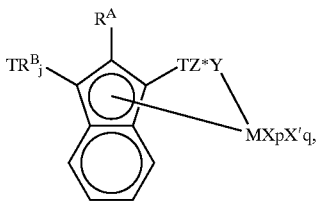

IV where T, $R^A$, $R^B$, j, M, X, X', p and q are as previously defined with respect to formula I, Y is —O—, —S—, —NR*—, or —PR*—;

Z* is SiR*$_2$, CR*$_2$, SiR*$_2$SiR*$_2$, CR*$_2$CR*$_2$, CR*=CR*, CR*$_2$SiR*$_2$, CR*$_2$SiR*$_2$CR*$_2$, SiR*$_2$CR*$_2$, SiR*$_2$CR*$_2$SiR*$_2$, CR*$_2$CR*$_2$SiR*$_2$, CR*$_2$CR*$_2$CR*$_2$, or GeR*$_2$; and R* independently each occurrence is hydrogen, or a member selected from hydrocarbyl, hydrocarbyloxy, silyl, halogenated alkyl, halogenated aryl, and combinations thereof, said R* having up to 20 nonhydrogen atoms, and optionally, two R* groups from Z, or an R* group from Z and an R* group from Y form a ring system.

A variety of metals can be used in the preparation of the metal complexes of this invention. Desirably M is a metal from one of Groups 3 to 13 of the Periodic Table of the Elements, the lanthanides or actinides, which is in the +2, +3 or +4 formal oxidation state, more desirably M is a metal from one of Groups 3 to 13. Most preferably, M is a metal from Group 4. Titanium is the most highly preferred metal. The ligands X and X' preferably are different depending on the metal oxidation state. More particularly, when p is 2, q is zero, M is in the +4 formal oxidation state, and X preferably s independently each occurrence chloride, methyl, benzyl, trimethylsilylmethyl, allyl, cyclopentadienyl, pyrollyl or two X groups together are 1,4-butane-diyl, 2-butene-1,4-diyl, 2,3-dimethyl-2-butene-1,4-diyl, 2-methyl-2-butene-1,4-diyl, or xylyldiyl. When p is 1, q is zero, M is in the +3 formal oxidation state, and X is preferably 2-(N, N-dimethyl)aminobenzyl, 2-(N,N-dimethylaminomethyl)phenyl, allyl, methallyl, trimethylsilylallyl. Finally, when p is 0, q is 1, M is in the +2 formal oxidation state, and X' is 1,4-diphenyl-1,3-butadiene, 1,3-pentadiene or 2,4-hexadiene.

In another aspect of this invention it is preferred that Y is —NR*, with the more preferred —NR* being those where R* is a group having a primary or secondary carbon atom bonded to N. Highly preferred are complexes where R* is cyclohexyl or isopropyl, and $TR^B_j$ is N,N-dimethylamino, pyrrolidino, or methoxy.

The complexes can be prepared by use of well-known synthetic techniques. Optionally a reducing agent can be employed to produce the lower oxidation state complexes. Such a process is disclosed in U.S. Pat. No. 5,470,993. The reactions are conducted in a suitable noninterfering solvent at a temperature from −100 to 300° C., preferably from −78 to 100° C., most preferably from 0 to 50° C. By the term "reducing agent" herein is meant a metal or compound which, under reducing conditions, causes the metal M to be reduced from a higher to a lower oxidation state. Examples of suitable metal reducing agents are alkali metals, alkaline earth metals, aluminum and zinc, alloys of alkali metals or alkaline earth metals such as sodium/mercury amalgam and sodium/potassium alloy. Examples of suitable reducing agent compounds are sodium naphthalenide, potassium graphite, lithium alkyls, lithium or potassium alkadienyls; and Grignard reagents. Most preferred reducing agents are the alkali metals or alkaline earth metals, especially lithium or magnesium metal and n-butyllithium.

Suitable reaction media for the formation of the complexes include aliphatic and aromatic hydrocarbons, ethers, and cyclic ethers, particularly branched-chain hydrocarbons such as isobutane, butane, pentane, hexane, heptane, octane, and mixtures thereof; cyclic and alicyclic hydrocarbons such as cyclohexane, cycloheptane, methylcyclohexane, methylcycloheptane, and mixtures thereof; aromatic and hydrocarbyl-substituted aromatic compounds such as benzene, toluene, and xylene, $C_{1-4}$ dialkyl ethers, $C_{1-4}$ dialkyl ether derivatives of (poly)alkylene glycols, and tetrahydrofuran. Mixtures of the foregoing are also suitable.

The compounds may be prepared by condensation of ketones with an amine or alcohol using standard synthetic techniques. Condensation with amines is well known from the teachings of W. E. Noland, V. Kameswaran J. Org. Chem. 1981, 46, 1940–1944, and elsewhere. An acid catalyst such as p-toluene sulfonic acid may be employed, and the water by-product is desirably azeotropically removed using a benzene or toluene solvent under reflux conditions. A similar technique has been disclosed in O. Cervinka, The Chemistry of Enamines, Part 1, Ch. 9; Z. Rappoport, Ed.; Wiley Interscience, New York, 1994, 468–500. With more sterically-hindered ketones or more volatile amines, such as dimethyl amine, it may be preferable to employ stronger dehydrating reagents such as titanium chloroamides, which may be generated in situ from titanium tetrachloride and the condensation amine. This technique has been previously disclosed in R. Carlson, A. Nilsson, *Acta Chemica Scandinavica*, B 38, 1984, 49–53.

Subsequent formation of the substituted ligand groups and ultimately the metal complexes themselves uses conventional organometallic synthetic procedures. Neutral amino-substituted complexes may be prepared directly by contacting a ketone with titanium tetraamide in an inert diluent at a temperature from 25 to 150° C.

Desirably, the substituted cyclopentadienes and intermediates prepared according to the invention are highly pure and free of ketone starting reactants, Aldol by-products, and higher weight reaction products which typically accompany product formation. Desirably the intermediate products may be subjected to purification procedures such as chromatographic purification, distillation, recrystallization, or other suitable technique to produce the desired purity in the final product. Rapid distillation of polyamine compounds is preferred to prevent thermal polymerization at elevated temperatures.

Conversion of the substituted cyclopentadienyl ligand to its corresponding anionic salt may be accomplished by reaction with an appropriate base of suitable strength in an appropriate noninterfering solvent. Under anaerobic, anhydrous conditions, the salt may be filtered, washed and dried in nearly quantitative yield.

The formation of ligands containing the -Z-functional group from the substituted cyclopentadiene metal compounds may be accomplished by reaction with an electrophile such as a halogenated secondary alkylamine or halogenated secondary silylamine to give the corresponding alkylamine or silylamine substituted compound. Suitable halogenated secondary alkylamines or halogenated secondary silylamines include (t-butyl) (chlorodimethylsilyl) amine, (t-butyl) (chlorodimethylsilylmethyl)amine, (t-butyl) (bromomethyldimethylsilyl)-amine, (t-butyl) (2-chloroethyl)amine, (chlorodimethylsilyl)(phenyl)amine, (adamantyl)(chlorodiphenylsilyl)-amine, (chlorodimethylsilyl) (cyclohexyl)amine, (benzyl) (chlorodimethylsilyl)amine and (t-butyl)(chloromethylphenylsilyl)amine. The technique is based upon the anion alkylation method previously disclosed by WO 93/08199 and *Organometallics*, 1996, 15(6), 1572–81. In a preferred embodiment, the lithio derivative of the anionic salt is slowly added to a molar excess of (t-butyl) (chlorodimethylsilyl) amine in an ether solvent. This ligand may also be converted to its insoluble anionic salt by reaction of the free base with two equivalents of a base of suitable strength in an appropriate noninterfering solvent.

By appropriate noninterfering solvent in the context of the present invention is meant a solvent that doesn't interfere with the formation of, or react deleteriously with, the desired product. Such solvents suitable for the preparation of the anionic salts of the invention include, but are not limited to aliphatic and aromatic hydrocarbons, particularly straight and branched chain hydrocarbons such as butane, pentane, hexane, heptane, octane, decane, including their branched isomers and mixtures thereof; cyclic and alicyclic hydrocarbons such as cyclohexane, cycloheptane, methylcyclohexane, methylcycloheptane and mixtures thereof; aromatic and hydrocarbyl-substituted aromatic compounds such as benzene, toluene, xylene, ethylbenzene, diethylbenzene and mixtures thereof; ethers and cyclic ethers, particularly $C_{1-6}$ dialkyl ethers, such as diethyl ether, dibutyl ether and methyl-t-butyl ether, $C_{1-6}$ dialkyl ether derivatives of (poly)alkylene glycols, such as dimethoxyethane, and dioxane and THF and mixtures thereof. Mixtures of the foregoing are also suitable.

Bases of suitable strength for the preparation of the dianionic salts of the invention include hydrocarbyl salts of Group 1 and Group 2 metals, especially alkyl or aryl salts of lithium or magnesium, such as methyllithium, ethyllithium, n-butyllithium, s-butyllithium, t-butyllithium, phenyllithium, methyl magnesium chloride, ethyl magnesium bromide, i-propyl magnesium chloride, dibutylmagnesium, (butyl)(ethyl)magnesium, dihexylmagnesium; Group 1 or Group 2 metals, such as lithium, sodium, potassium and magnesium; Group 1, Group 2 or Group 13 metal hydrides, such as lithium hydride, sodium hydride, potassium hydride or lithium aluminum hydride; Group 1 or Group 2 metal amide complexes, such as lithium diisopropylamide, lithium dimethylamide, lithium hexamethyidisilazide, sodamide and magnesium diisopropylamide.

Bases of suitable strength for the preparation of the anionic salts of the invention include the foregoing as well as Group 1 or Group 2 metal alkoxide complexes, such as sodium ethoxide, sodium t-butoxide, potassium butoxide and potassium amylate.

The metallation of the dianionic salt may be accomplished by methods cited in this art as well. Reaction of the dianionic salt with $TiCl_3$ (THF) 3, followed by oxidation with methylene chloride or lead dichloride, substantially according to the technique of *Chem. Ber.*, 1996, 129, 1429–1431 or EP-A-514,828 affords the titanium (IV) dichloride complex in very high yield. The dichloride may thereafter be silylated or hydrocarbylated by ligand exchange with an appropriate silylating or hydrocarbylating agent, such as methyllithium, methyl magnesium chloride, benzyl potassium, allyl lithium, trimethylsilylmethyl lithium, neopentyl magnesium bromide and phenyllithium.

A general method for producing the titanium(II) diene complex from the corresponding titanium(IV) dichloride preferably involves the treatment of the dichloride with n-butyl lithium in the presence of an appropriate diene. A similar technique has been described in *Organometallics*, 1995, 14, 3132–3134 as well as in U.S. Pat. No. 5,556,928.

The formation of the metal complexes wherein the metal is in the +3 formal oxidation state according to the invention can be accomplished by any of several synthesis methods. One technique involves the reaction under anaerobic and anhydrous conditions of the dianionic salts with trivalent metal salts, such as Group 4 metal (III) halide or alkoxide complexes, optionally followed by silylation or hydrocarbylation with suitable silylating or hydrocarbylating agents, to form the corresponding halide, alkoxide, silyl or hydrocarbyl complexes of the invention. A further synthesis method involves reducing an appropriate metal (IV) complex with a suitable reducing agent to the corresponding metal (III) complex. Suitable reducing agents especially include zinc, aluminum, lithium and magnesium.

Suitable silylating and hydrocarbylating agents for the metal complexes of the invention include the corresponding silyl or hydrocarbyl derivatives of Group 1, 2 or 13 metals or Group 2 metal halides, preferably lithium sodium, potassium, magnesium and aluminum, or Group 2 metal Grignards. Examples of suitable hydrocarbyl and silyl groups include alkyl, such as methyl, ethyl, propyl, butyl, neopentyl and hexyl; aryl, such as phenyl, naphthyl and biphenyl; aralkyl, such as benzyl, tolylmethyl, diphenylmethyl; alkaryl, such as tolyl and xylyl; allyl; silyl- or alkyl-substituted allyl, such as methylallyl, trimethylsilylallyl, dimethylallyl and trimethylallyl; trialkylsilyl, such as trimethylsilyl and triethylsilyl; trialkylsilylalkyl, such as trimethylsilylmethyl; pentadienyl; alkyl- or silyl-substituted pentadienyl, such as methylpentadienyl, dimethylpentadienyl, trimethylsilylpentadienyl, bis (trimethylsilyl)pentadienyl, cyclohexadienyl and dimethylcyclohexadienyl; dialkylaminoalkaryl, such as o-(N,N-dimethylaminomethyl)phenyl; and dialkylaminoaralkyl, such as o-(N,N-dimethylamino)benzyl. Preferred silylating and hydrocarbylating agents include trimethylaluminum, methyllithium, methyl magnesium chloride, neopentyllithium, trimethylsilylmethyl magnesium chloride and phenyllithium. Stabilizing group-containing hydrocarbylating agents are also included, especially the stabilizing group-containing hydrocarbylating agents and salts of the stabilizing group-containing hydrocarbyl groups described in U.S. Pat. No. 5,504,224, whose salts include, for example, benzyl potassium, 2-(N,N-dimethylamino)benzyllithium, allyllithium and dimethylpentadienyl potassium. Such stabilizing groups are further described in U.S. Pat. No. 5,374,696, and elsewhere.

The complexes are rendered catalytically active by combination with an activating cocatalyst or by use of an activating technique. Suitable activating cocatalysts for use herein include polymeric or oligomeric alumoxanes, especially methylalumoxane, triisobutyl aluminum modified methylalumoxane, or isobutylalumoxane; neutral Lewis acids, such as $C_{1-45}$ hydrocarbyl substituted Group 13 compounds, especially tri(hydrocarbyl)aluminum- or tri (hydrocarbyl)boron compounds and halogenated (including perhalogenated) derivatives thereof, having from 1 to 15 carbons in each hydrocarbyl or halogenated hydrocarbyl group, more especially perfluorinated tri(aryl)boron compounds, and most especially tris(o-nonafluorobiphenyl) borane, tris(pentafluorophenyl)borane; nonpolymeric, compatible, noncoordinating, ion forming compounds (including the use of such compounds under oxidizing conditions), especially the use of ammonium-, phosphonium-, oxonium-, carbonium-, silylium- or sulfonium-salts of compatible, noncoordinating anions, or ferrocenium salts of compatible, noncoordinating anions; bulk electrolysis (explained in more detail hereinafter); and combinations of the foregoing activating cocatalysts and techniques. The foregoing activating cocatalysts and activating techniques have been previously taught with respect to different metal complexes in EP-A-277,003 and U.S. Pat. No. 5,153,157, U.S. Pat. No. 5,064,802, U.S. Pat. No. 5,321,106, and U.S. Pat. No. 5,721,185.

Combinations of neutral Lewis acids, especially the combination of a trialkyl aluminum compound having from 1 to 4 carbons in each alkyl group and a halogenated tri (hydrocarbyl)boron compound having from 1 to 20 carbons in each hydrocarbyl group, especially tris (pentafluorophenyl)borane, tris(o-nonafluorobiphenyl) borane, further combinations of such neutral Lewis acid mixtures with a polymeric or oligomeric alumoxane, and combinations of a single neutral Lewis acid, especially tris(pentafluorophenyl)borane with a polymeric or oligomeric alumoxane are especially desirable activating cocatalysts. A benefit according to the present invention is the discovery that the most efficient catalyst activation using such a combination of tris(pentafluorophenyl)borane/alumoxane mixture occurs at reduced levels of alumoxane. Preferred molar ratios of metal complex: tris (pentafluorophenyl)borane: alumoxane are from 1:1:1 to 1:5:5, more preferably from 1:1:1.5 to 1:5:3. The surprising efficient use of lower levels of alumoxane with the present invention allows for the production of olefin polymers with high catalytic efficiencies using less of the expensive alumoxane cocatalyst. Additionally, polymers with lower levels of aluminum residue, and hence greater clarity, are obtained.

Suitable ion forming compounds useful as cocatalysts in one embodiment of the present invention comprise a cation which is a Bronsted acid capable of donating a proton, and a compatible, noncoordinating anion, A. As used herein, the term "noncoordinating" means an anion or substance which either does not coordinate to the metal complex and the catalytic derivative derived therefrom, or which is only weakly coordinated to such complexes thereby remaining sufficiently labile to be displaced by a neutral Lewis base. A noncoordinating anion specifically refers to an anion which when functioning as a charge balancing anion in a cationic metal complex does not transfer an anionic substituent or fragment thereof to said cation thereby forming neutral complexes. "Compatible anions" are anions which are not degraded to neutrality when the initially formed complex decomposes and are noninterfering with desired subsequent polymerization or other uses of the complex.

Preferred anions are those containing a single coordination complex comprising a charge-bearing metal or metalloid core which anion is capable of balancing the charge of the active catalyst species (the metal cation) which may be formed when the two components are combined. Also, said anion should be sufficiently labile to be displaced by olefinic, diolefinic and acetylenically unsaturated compounds or other neutral Lewis bases such as ethers or nitrites. Suitable metals include, but are not limited to, aluminum, gold and platinum. Suitable metalloids include, but are not limited to, boron, phosphorus, and silicon. Compounds containing anions which comprise coordination complexes containing a single metal or metalloid atom are, of course, well known and many, particularly such compounds containing a single boron atom in the anion portion, are available commercially.

Preferably such cocatalysts may be represented by the following general formula:

$$(L^*-H)^+_d(A)^{d-}$$

wherein:

L* is a neutral Lewis base;

$(L^*-H)^+$ is a Bronsted acid;

$(A)^{d-}$ is a noncoordinating, compatible anion having a charge of d-, and d is an integer from 1 to 3.

More preferably $(A)^{d-}$ corresponds to the formula: $[M'Q_4]$;

wherein:

M' is boron or aluminum in the +3 formal oxidation state; and

Q independently each occurrence is selected from hydride, dialkylamido, halide, hydrocarbyl, hydrocarbyloxide, halosubstituted-hydrocarbyl, halo-substituted hydrocarbyloxy, and halo-substituted silylhydrocarbyl radicals (including perhalogenated hydrocarbyl-perhalogenated hydrocarbyloxy- and perhalogenated silylhydrocarbyl radicals), said Q having up to 20 carbons with the proviso that in not more than one occurrence is Q halide. Examples of suitable hydrocarbyloxide Q groups are disclosed in U.S. Pat. No. 5,296,433.

In a more preferred embodiment, d is one, that is, the counter ion has a single negative charge and is A⁻. Activating cocatalysts comprising boron which are particularly useful in the preparation of catalysts of this invention may be represented by the following general formula:

$$(L^*-H)^+(BQ_4)^-;$$

wherein:

L* is as previously defined;

B is boron in a formal oxidation state of 3; and

Q is a hydrocarbyl-, hydrocarbyloxy-, fluorinated hydrocarbyl-, fluorinated hydrocarbyloxy-, or fluorinated silylhydrocarbyl- group of up to 20 nonhydrogen atoms, with the proviso that in not more than one occasion is Q hydrocarbyl.

Most preferably, Q is each occurrence a fluorinated aryl group, especially, a pentafluorophenyl group.

Illustrative, but not limiting, examples of ion forming compounds comprising proton donatable cations which may be used as activating cocatalysts in the preparation of the catalysts of this invention are tri-substituted ammonium salts such as:

trimethylammonium tetraphenylborate, methyldioctadecylammonium tetraphenylborate, triethylammonium tetraphenylborate, tripropylammonium tetraphenylborate, tri(n-butyl)ammonium tetraphenylborate, methyltetradecyloctadecylammonium tetraphenylborate, N,N-dimethylanilinium tetraphenylborate, N,N-diethylanilinium tetraphenylborate, N,N-dimethyl(2,4,6-trimethylanilinium) tetraphenylborate, trimethylammonium tetrakis(penta-fluorophenyl)borate, triethylammonium tetrakis(pentafluorophenyl)borate, tripropylammonium tetrakis(pentafluorophenyl)borate, tri(n-butyl)ammonium tetrakis(pentafluorophenyl)borate, tri(sec-butyl)ammonium tetrakis(pentafluorophenyl)borate, N,N-dimethylanilinium tetrakis(pentafluorophenyl)borate, N,N-diethylanilinium tetrakis(pentafluorophenyl)borate, N,N-dimethyl(2,4,6-trimethylanilinium) tetrakis(pentafluorophenyl)borate, trimethylammonium tetrakis(2,3,4,6-tetrafluorophenyl)borate, triethylammonium tetrakis(2,3,4,6-tetrafluorophenyl)borate, tripropylammonium tetrakis(2,3,4,6-tetrafluorophenyl)borate, tri(n-butyl)ammonium tetrakis(2,3,4,6-tetrafluorophenyl)borate, dimethyl(t-butyl)ammonium tetrakis(2,3,4,6-tetrafluorophenyl)borate, N,N-dimethylanilinium tetrakis(2,3,4,6-tetrafluorophenyl)borate, N,N-diethylanilinium tetrakis(2,3,4,6-tetrafluorophenyl)borate, and N,N-dimethyl-(2,4,6-trimethylanilinium) tetrakis-(2,3,4,6-tetrafluorophenyl)borate.

Dialkyl ammonium salts such as:

di-(i-propyl)ammonium tetrakis(pentafluorophenyl)borate, and dicyclohexylammonium tetrakis(pentafluorophenyl)borate.

Tri-substituted phosphonium salts such as:

triphenylphosphonium tetrakis(pentafluorophenyl)borate, tri(o-tolyl)phosphonium tetrakis(pentafluorophenyl)borate, and tri(2,6-dimethylphenyl)phosphonium tetrakis(pentafluorophenyl)borate.

Preferred are tetrakis(pentafluorophenyl)borate salts of long chain alkyl mono- and disubstituted ammonium complexes, especially $C_{14}$–$C_{20}$ alkyl ammonium complexes, especially methyldi(octadecyl)ammonium tetrakis(pentafluorophenyl)borate and methyldi(tetradecyl)ammonium tetrakis(pentafluorophenyl)borate.

Especially preferred activating cocatalysts are tris(pentafluorophenyl)borane, $(R^1_2NHCH_3)^+(C_6H_4OH)B(C_6F_5)_3^-$, $(R^1_2NHCH_3)^+B(C_6F_5)_4^-$, or $[(C_6H_5)NHR^2_2]^+B(C_6F_5)_4^-$, where $R^1$ independently each occurrence is a substituted or unsubstituted saturated hydrocarbyl group having from 12 to 30 carbon atoms, and $R^2$ independently each occurrence is a substituted or unsubstituted saturated hydrocarbyl group having from 1 to 8 carbon atoms.

Another suitable ion forming, activating cocatalyst comprises certain imidazolide, substituted imidazolide, imidazolinide, substituted imidazolinide, benzimidazolide, or substituted benzimidazolide anions depicted schematically as follows:

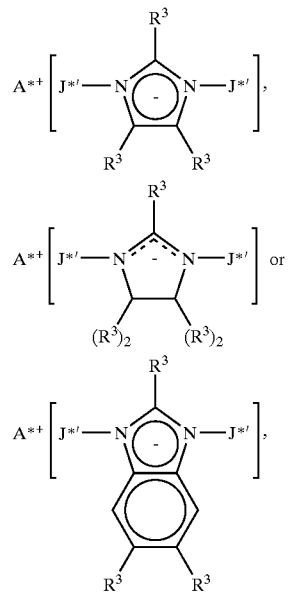

wherein:

$A^{**}$ is a monovalent cation, preferably a trihydrocarbyl ammonium cation, containing one or two $C_{10-40}$ alkyl groups, especially the methylbis(tetradecyl)ammonium- or methylbis(octadecyl)ammonium-cation, $R^3$, independently each occurrence, is hydrogen or a halo, hydrocarbyl, halocarbyl, halohydrocarbyl, silylhydrocarbyl, or silyl, (including mono-, di- and tri(hydrocarbyl)silyl) group of up to 30 atoms not counting hydrogen, preferably $C_{1-20}$ alkyl, and $J^{*'}$ is tris(pentafluorophenyl)borane or tris(pentafluorophenyl)alumane).

Another suitable ion forming, activating cocatalyst comprises a salt of a cationic oxidizing agent and a noncoordinating, compatible anion represented by the formula:

$$(OX^{e+})_d(A^{d-})_e$$

wherein:

$OX^{e+}$ is a cationic oxidizing agent having a charge of e+;

e is an integer from 1 to 3; and $A^{d-}$ and d are as previously defined.

Examples of cationic oxidizing agents include: ferrocenium, hydrocarbyl-substituted ferrocenium, $Ag^+$ and $Pb^{+2}$. Preferred embodiments of $A^{d-}$ are those anions previously defined with respect to the Bronsted acid containing activating cocatalysts, especially tetrakis (pentafluorophenyl)borate.

Another suitable ion forming, activating cocatalyst comprises a compound which is a salt of a carbenium ion and a noncoordinating, compatible anion represented by the formula:

$$\text{\textcopyright}^+A^-$$

wherein:

$\text{\textcopyright}^+$ is a $C_{1-20}$ carbenium ion; and $A^-$ is as previously defined. A preferred carbenium ion is the trityl cation, that is, triphenylmethylium.

A further suitable ion forming, activating cocatalyst comprises a compound which is a salt of a silylium ion and a noncoordinating, compatible anion represented by the formula:

$$R_3Si^+A^-$$

wherein:

R is $C_{1-10}$ hydrocarbyl, and $A^-$ are as previously defined.

Preferred silylium salt activating cocatalysts are trimethylsilylium tetrakispentafluorophenylborate, triethylsilylium tetrakispentafluorophenylborate and ether substituted adducts thereof. Silylium salts have been previously generically disclosed in *J. Chem Soc. Chem. Comm.*, 1993, 383–384, as well as Lambert, J. B., et al., *Organometallics*, 1994, 13, 2430–2443. The use of the above silylium salts as activating cocatalysts for addition polymerization catalysts is disclosed in U.S. Pat. No. 5,625,087.

Certain complexes of alcohols, mercaptans, silanols, and oximes with tris(pentafluorophenyl)borane are also effective catalyst activators and may be used according to the present invention. Such cocatalysts are disclosed in U.S. Pat. No. 5,296,433.

The technique of bulk electrolysis involves the electrochemical oxidation of the metal complex under electrolysis conditions in the presence of a supporting electrolyte comprising a noncoordinating, inert anion. In the technique, solvents, supporting electrolytes and electrolytic potentials for the electrolysis are used such that electrolysis byproducts that would render the metal complex catalytically inactive are not substantially formed during the reaction. More particularly, suitable solvents are materials that are: liquids under the conditions of the electrolysis (generally temperatures from 0 to 100° C.), capable of dissolving the supporting electrolyte, and inert. "Inert solvents" are those that are not reduced or oxidized under the reaction conditions employed for the electrolysis. It is generally possible in view of the desired electrolysis reaction to choose a solvent and a supporting electrolyte that are unaffected by the electrical potential used for the desired electrolysis. Preferred solvents include difluorobenzene (all isomers), dimethoxyethane (DME), and mixtures thereof.

The electrolysis may be conducted in a standard electrolytic cell containing an anode and cathode (also referred to as the working electrode and counter electrode respectively). Suitable materials of construction for the cell are glass, plastic, ceramic and glass coated metal. The electrodes are prepared from inert conductive materials, by which are meant conductive materials that are unaffected by the reaction mixture or reaction conditions. Platinum or palladium are preferred inert conductive materials. Normally an ion permeable membrane such as a fine glass frit separates the cell into separate compartments, the working electrode compartment and counter electrode compartment. The working electrode is immersed in a reaction medium comprising the metal complex to be activated, solvent, supporting electrolyte, and any other materials desired for moderating the electrolysis or stabilizing the resulting complex. The counter electrode is immersed in a mixture of the solvent and supporting electrolyte. The desired voltage may be determined by theoretical calculations or experimentally by sweeping the cell using a reference electrode such as a silver electrode immersed in the cell electrolyte. The background cell current, the current draw in the absence of the desired electrolysis, is also determined. The electrolysis is completed when the current drops from the desired level to the background level. In this manner, complete conversion of the initial metal complex can be easily detected. Suitable supporting electrolytes are salts comprising a cation and a compatible, noncoordinating anion, $A^-$.

Preferred supporting electrolytes are salts corresponding to the formula $G^+A^-$; wherein:

$G^+$ is a cation which is nonreactive towards the starting and resulting complex, and $A^-$ is as previously defined.

Examples of cations, $G^+$, include tetrahydrocarbyl substituted ammonium or phosphonium cations having up to 40 nonhydrogen atoms. Preferred cations are the tetra(n-butylammonium)- and tetraethylammonium-cations.

During activation of the complexes of the present invention by bulk electrolysis the cation of the supporting electrolyte passes to the counter electrode and $A^-$ migrates to the working electrode to become the anion of the resulting oxidized product. Either the solvent or the cation of the supporting electrolyte is reduced at the counter electrode in equal molar quantity with the amount of oxidized metal complex formed at the working electrode. Preferred supporting electrolytes are tetrahydrocarbylammonium salts of tetrakis(perfluoroaryl) borates having from 1 to 10 carbons in each hydrocarbyl or perfluoroaryl group, especially tetra(n-butylammonium)tetrakis-(pentafluorophenyl) borate.

A further recently discovered electrochemical technique for generation of activating cocatalysts is the electrolysis of a disilane compound in the presence of a source of a noncoordinating compatible anion. This technique is more fully disclosed in U.S. Pat. No. 5,372,682.

The foregoing electrochemical activating technique and activating cocatalysts may also be used in combination. An especially preferred combination is a mixture of a tri(hydrocarbyl)aluminum or tri(hydrocarbyl)borane compound having from 1 to 4 carbons in each hydrocarbyl group with an oligomeric or polymeric alumoxane compound.

The molar ratio of catalyst/cocatalyst employed preferably ranges from 1:10,000 to 100:1, more preferably from 1:5000 to 10:1, most preferably from 1:1000 to 1:1. Alumoxane, when used by itself as an activating cocatalyst, is employed in large quantity, generally at least 100 times the quantity of metal complex on a molar basis. Tris(pentafluorophenyl)borane, where used as an activating cocatalyst, is employed in a molar ratio to the metal complex of form 0.5:1 to 10:1, more preferably from 1:1 to 6:1, most preferably from 1:1 to 5:1. The remaining activating cocatalysts are generally employed in approximately equimolar quantity with the metal complex.

Suitable polymerizable monomers include ethylenically unsaturated monomers, acetylenic compounds, conjugated or nononjugated dienes, and polyenes. Preferred monomers include olefins, for examples alpha-olefins having from 2 to 20,000, preferably from 2 to 20, more preferably from 2 to 8 carbon atoms and combinations of two or more of such alpha-olefins. Particularly suitable alpha-olefins include, for example, ethylene, propylene, 1-butene, 1-pentene, 4-methylpentene-1,1-hexene, 1-heptene, 1-octene, 1-nonene, 1-decene, 1-undecene, 1-dodecene, 1-tridecene, 1-tetradecene, 1-pentadecene, or combinations thereof, as well as long chain vinyl terminated oligomeric or polymeric reaction products formed during the polymerization, and $C_{10-30}$ α-olefins specifically added to the reaction mixture in order to produce relatively long chain branches in the resulting polymers. Preferably, the alpha-olefins are ethylene, propene, 1-butene, 4-methyl-pentene-1,1-hexene, 1-octene, and combinations of ethylene and/or propene with one or more of such other alpha-olefins. Other preferred monomers include styrene, halo- or alkyl substituted styrenes, tetrafluoroethylene, vinylcyclobutene, 1,4-hexadiene, dicyclopentadiene, ethylidene norbornene, and 1,7-octadiene. Mixtures of the above-mentioned monomers may also be employed.

In general, the polymerization may be accomplished at conditions well known in the prior art for solution phase, slurry, gas phase and high pressure Ziegler-Natta or Kaminsky-Sinn type polymerization reactions. Examples of such well known polymerization processes are depicted in U.S. Pat. No. 5,084,534, U.S. Pat. No. 5,405,922, U.S. Pat. No. 4,588,790, U.S. Pat. No. 5,032,652, U.S. Pat. No. 4,543,399, U.S. Pat. No. 4,564,647, U.S. Pat. No. v4,522,987, and elsewhere. Preferred polymerization temperatures are from 0–250° C. Preferred polymerization pressures are from atmospheric to 3000 atmospheres. Molecular weight control agents can be used in combination with the present cocatalysts. Examples of such molecular weight control agents include hydrogen, silanes or other known chain transfer agents. The catalyst composition may be used by itself (homogeneously) or supported on an inert support such as silica, alumina or a polymer.

The skilled artisan will appreciate that the invention disclosed herein may be practiced in the absence of any component which has not been specifically disclosed. The following examples are provided as further illustration of the invention and are not to be construed as limiting. Unless stated to the contrary all parts and percentages are expressed on a weight basis. Where stated, the term "room temperature" refers to a temperature from 20 to 25° C., the term "overnight" refers to a time from 12 to 18 hours, and the term "mixed alkanes" refers to a mixture of propylene oligomers sold by Exxon Chemicals Inc. under the trade designation Isopart™ E.

$^1$H and $^{13}$C NMR spectra were recorded on a Varian XL (300 MHz) spectrometer. Chemical shifts were determined relative to TMS or through the residual CHCl$_3$ in CDCl$_3$ or the residual C$_6$HD$_5$ in C$_6$D$_6$, relative to TMS. Tetrahydrofuran (THF), diethylether, toluene, and hexane were used following passage through double columns charged with activated alumina and alumina supported mixed metal oxide catalyst (Q-5® catalyst, available from Engelhard Corp.). The compounds n-BuLi, Grignard reagents were all used as purchased from Aldrich Chemical Company. All syntheses were performed under dry nitrogen atmosphere using a combination of glove box and high vacuum techniques.

EXAMPLE 1

Preparation of Dichloro(N-(1,1-dimethylethyl)-1,1-dimethyl-1-((1,2,3,3a,7a-η)-1H-inden-1-yloxy) silanaminato(1-)-titanium Step 1 Preparation of N-(tert-Butyl)-N-(1-(1H-3-indenyloxy)-1,1-dimethylsilyl)amine. 1-

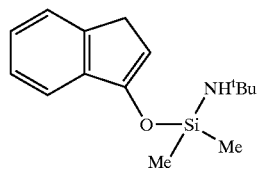

Indanone (3.32 g, 25.1 mmol) was dissolved in 100 mL of THF and the solution was cooled to −78° C. To this solution 17.5 mL of a 1.50 M solution of lithium bis isopropoxyamide (LDA) (26.4 mmol) was added within 10 min. The resulting dark yellow-green solution was stirred for 1 hr. and then 5.00 g (30.1 mmol) of N-(tert-butyl)-N-(1-chloro-1,1-dimethylsilyl)amine was added within 10 min. The mixture was stirred for 1 h at −78° C. The flask was allowed to warm to room temperature where it was stirred for another 2 hr. Solvent was removed under reduced pressure and the residue was extracted with 40 mL of hexane and filtered. Again solvent was removed under reduced pressure leaving 6.51 g of the product as a yellow liquid. Yield was 99 percent.

$^1$H (C$_6$D$_6$) δ 0.27 (s, 6H), 1.15 (s, 9H), 3.11 (d, 2H, $^3J_{H-H}$=1.8 Hz), 5.42 (s, 1H), 7.14 (t, 1H, $^3J_{H-H}$=7.22 Hz), 7.25 (m, 2H), 7.64 (d, $^3J_{H-H}$=7.56 Hz). $^{13}$C{$^1$H}(C$_6$D$_6$) δ 0.37, 33.67, 34.45, 49.66, 105.51, 118.69, 124.07, 125.49, 126.43, 142.64, 142.93, 153.99.

Step 2 Preparation of N-(tert-Butyl)-N-(1-(1H-3-indenyloxy)-1,1-dimethylsilyl)amine, Dilithium Salt

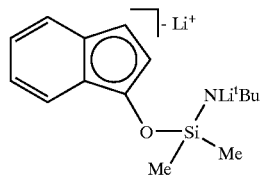

In the drybox 3.67 g (14.04 mmol) of N-(tert-butyl)-N-(1-(1H-3-indenyloxy)-1,1-dimethylsilyl)amine was combined with 60 mL of hexane. To this solution 19 mL (32.3 mmol) of t-BuLi (1.7 M) was added dropwise. Upon complete addition of the t-BuLi, the solution was stirred overnight. The resulting precipitate was collected via filtration and washed with hexane to give 2.76 g (72 percent yield) of the dilithium salt as a yellow solid.

Step 3 Preparation of Dichloro(N-(1,1-dimethylethyl)-1,1-dimethyl-1-((1,2,3,3a,7a-η)-1H-inden-1-yloxy)silanaminato(1-)-titanium

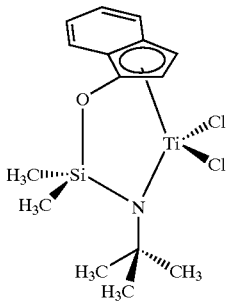

In a drybox 3.75 g (10.12 mmol) of TiCl$_3$(THF)$_3$ was suspended in 50 mL of THF. To this solution 2.76 g (10.12 mmol) of N-(tert-butyl)-N-(1-(1H-3-indenyloxy)-1,1-dimethylsilyl)amine, dilithium salt dissolved in 50 mL of THF was added within 2 min. The solution was then stirred for 45 min. After this time 1.83 g of PbCl$_2$ (6.58 mmol) was added and the solution was stirred for 50 min. The THF was then removed under reduced pressure. The residue was extracted with 40 mL of toluene, the solution was filtered, and the toluene was removed under reduced pressure. The residue was titrated with 40 mL of hexane and the precipitate was collected via filtration on a frit, washed with hexane and dried under vacuum to yield 2.23 g (58 percent yield) of the titanium dichloride.

$^1$H (C$_6$D$_6$) δ 0.35 (s, 3H), 0.42 (s, 3H), 1.42 (s, 9H), 5.91 (d, 1H, $^3J_{H-H}$=3.4 Hz), 6.24 (d, 1H, $^3J_{H-H}$=3.2 Hz), 6.84 (t, 1H, $^3J_{H-H}$=7.5 Hz), 6.96 (t, 1H, $^3J_{H-H}$=7.6 Hz), 7.10 (d, 1H, $^3J_{H-H}$=8.5 Hz), 7.41 (d, 1H, $^3J_{H-H}$=8.5 Hz). $^{13}$C{$^1$H}(C$_6$D$_6$) δ 5.45, 5.99, 33.16, 61.54 111.87, 121.58, 121.81, 126.68, 127.25, 129.12, 145.97.

EXAMPLE 2

Preparation of (N-(1,1-Dimethylethyl)-1,1-dimethyl-1-((1,2,3,3a,7a-η)-1H-inden-1-yloxy)silanaminato(1-)dimethyl-titanium

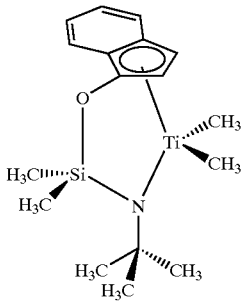

In a drybox 0.600 g (1.59 mmol) of dichloro(N-(1,1-dimethylethyl)-1,1-dimethyl-1-((1,2,3,3a,7a-η)-1H-inden-1-yloxy)silanaminato(1-)-titanium was dissolved in 40 mL of Et$_2$O. To this solution 1.11 mL (3.33 mmol) of MeMgI (3.0 M) was added dropwise while stirring over a 5 minute period. The solution changed colorfrom deep brown to yellow-green. After the addition of MeMgI was completed, the solution was stirred for 50 minutes. Et$_2$O was removed under reduced pressure and the residue was extracted with hexane (2×20 mL), the solution was filtered and the filtrate was evaporated to dryness under reduced pressure to give 0.40 g (75 percent yield) of the dimethyl titanium complex as a yellow solid.

$^1$H (C$_6$D$_6$) δ −0.00 (s, 3H), 0.39 (s, 3H), 0.44 (s, 3H), 0.89 (s, 3H), 1.54 (s, 9H), 5.73 (d, 1H, $^3J_{H-H}$=3.2 Hz), 6.19 (d, 1H, $^3J_{H-H}$=3.2 Hz), 6.78 (t, 1H, $^3J_{H-H}$=7.6 Hz), 6.97 (t, 1H, $^3J_{H-H}$=7.6 Hz), 7.24 (d, 1H, $^3J_{H-H}$=8.5 Hz), 7.36 (d, 1H, $^3J_{H-H}$=8.6 Hz). $^{13}$C{$^1$H}(c$_6$D$_6$) δ 5.87, 6.22, 34.80, 55.09, 56.92, 60.80, 98.74, 110.17, 119.24, 122.11, 122.59, 124.73, 125.78, 126.65, 136.73.

EXAMPLE 3

Preparation of Dichloro(N-(1,1-dimethylethyl)-1,1-dimethyl-1-(1,2,3,3a,7a-η)-1H-inden-2-yloxy)silanaminato(2-)-titanium Step 1 Preparation of N-(tert-Butyl)-N-(1-(1H-2-indenyloxy)-1,1-dimethylsilyl)amine

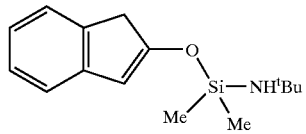

2-Indanone (3.32 g, 25.12 mmol) was dissolved in 100 mL of THF and the solution was cooled to −78° C. To this solution 17.5 mL of a 1.50 M solution of LDA (26.4 mmol) was added within 10 min. During the addition a white precipitate appeared in the flask. The reaction mixture was stirred for 1 h and then 5.00 g (30.1 mmol) of N-(tert-butyl)-N-(1-chloro-1,1-dimethylsilyl)amine was added within 10 min. The mixture was stirred 2 h at −78° C. and then the flask was warmed slowly to room temperature where in was stirred overnight. The solvent was then removed under reduced pressure and the residue was extracted with hexane (2×20 mL) and filtered. Solvent was removed under reduced pressure leaving 6.55 g of the silylamine as a yellow liquid. Yield was 99.7 percent.

$^1$H (C$_6$D$_6$) δ 0.19 (s, 6H), 1.09 (s, 9H), 3.25 (s, 2H), 5.96 (s, 1H), 7.0–7.23 (m, 4H). $^{13}$C{$^1$H}(C$_6$D$_6$) δ 0.30, 33.54, 40.08, 49.61, 106.98, 119.43, 122.85, 123.51, 126.96, 136.92, 145.86, 162.28.

Step 2 Preparation of N-(tert-Butyl)-N-(1-(1H-2-indenyloxy)-1,1-dimethylsilyl)amine, Dilithium Salt.

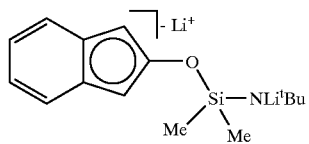

In a drybox 6.55 g (25.0 mmol) of N-(tert-butyl)-N-(1-(1H-2-indenyloxy)-1,1-dimethylsilyl)amine was combined with 90 mL of hexane. To this solution 36.8 mL (62.3 mmol) of t-BuLi (1.70 M) was added dropwise. Upon complete addition of the t-BuLi the solution was stirred overnight. The resulting off-white precipitate was collected via filtration, washed with 100 mL of hexane and dried under reduced pressure to give 5.57 g (81 percent yield) of the dilithium salt as an off-white solid.

Step 3 Preparation of Dichloro(N-(1,1-dimethylethyl)-1,1-dimethyl-1-((1,2,3,3a,7a-η)-1H-inden-2-yloxy)silanaminato(2-)-titanium

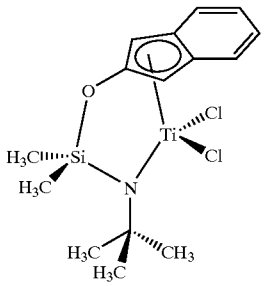

In a drybox 5.15 g (13.9 mmol) of TiCl$_3$(THF)$_3$ was suspended in 100 mL of THF. To this solution 3.80 g (13.9 mmol) of N-(tert-butyl)-N-(1-(1H-2-indenyloxy)-1,1-dimethylsilyl)amine dilithium salt dissolved in 50 mL of THF was added within 2 min. The solution was then stirred for 60 min. After this period 2.51 g of PbCl$_2$ (9.04 mmol) was added and the solution was stirred for 1 h. The THF was then removed under reduced pressure. The residue was then extracted with 40 mL of toluene, the solution was filtered, and the toluene was removed under reduced pressure. The residue was then titrated with 40 mL of hexane and the precipitate was collected via filtration, washed with hexane and dried under vacuum to yield 3.63 g (69 percent yield) of the titanium dichloride as an orange solid. X-ray analysis was consistent with the structure of the titanium dichloride. An ORTEP structure derived from such X-ray data is shown in FIG. 1.

$^1$H (C$_6$D$_6$) δ 0.35 (s, 6H), 1.46 (s, 9H), 6.04 (s, 2H), 6.98 (dd, 2H, $^3J_{H-H}$=6.5 Hz, $^4J_{H-H}$=3.1 Hz), 7.34 98 (dd, 2H, $^3J_{H-H}$=6.4 Hz, $^4J_{H-H}$=3.1 Hz). $^{13}$C{$^1$H}(C$_6$D$_6$) δ 5.18, 32.87, 63.55, 104.61, 123.19, 126.21, 153.23.

EXAMPLE 4

Preparation of (N-(1,1-Dimethylethyl)-1,1-dimethyl-1-((1,2,3,3a,7a-η)-1H-inden-2-yloxy)silanaminato(2-)-dimethyl-titanium

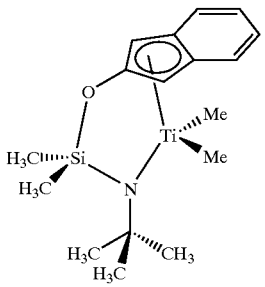

In a drybox 0.490 g (1.30 mmol) dichloro(N-(1,1-dimethylethyl)-1,1-dimethyl-1-((1,2,3,3a,7a-η)-1H-inden-2-yloxy)silanaminato(2-)-titanium was dissolved in 40 mL of Et$_2$O. To this solution 0.91 mL (2.72 mmol) of MeMgI (3.0 M) was added dropwise while stirring over a 5 minute period. The solution changed color from orange-brown to dark yellow. After the addition of MeMgI was completed, the solution was stirred for 50 minutes. Then the Et$_2$O was removed under reduced pressure and the residue was extracted with hexane (2×20 mL), the solution was filtered and the filtrate was evaporated to dryness under reduced pressure to give 0.385 g (88 percent yield) of the dimethyl titanium complex as a yellow solid.

$^1$H (C$_6$D$_6$) δ 0.32 (s, 6H), 0.41 (s, 6H), 1.59 (s, 9H), 5.84 (s, 2H), 7.04 (dd, 2H, $^3J_{H-H}$=6.5 Hz, $^3J_{H-H}$=3.1 Hz), 7.28 (dd, 2H, $^3J_{H-H}$=6.5 Hz, $^3J_{H-H}$=3.1 Hz). $^{13}$C{$^1$H}(C$_6$D$_6$) δ 5.26, 34.84, 57.83, 58.02, 97.60, 21.53, 124.81, 125.18, 146.82.

EXAMPLE 5

Preparation of Dichloro(N-(1,1-dimethylethyl)-1,1-dimethyl-1-((1,2,3,3a,7a-η)-2-methyl-1H-inden-1-yloxysilanaminato(1-)-titanium Step 1 Preparation of N-(tert-Butyl)-N-(1-(2-methyl-(1H-3-indenyloxy))-1,1-dimethylsilyl)amine.

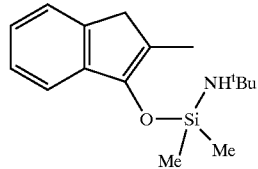

2-methyl-1-indanone (4.00 g, 27.36 mmol) was dissolved in 150 ml of THF and the solution was cooled to −78° C. To this solution 19.1 ml of 1.5 M solution of LDA (28.7 mmol) was added within 10 min resulting in a green solution that was stirred for 2 hr. and then 5.44 g (32.8 mmol) of ClSiMe$_2$—NHtBu was added within 10 min. The mixture was stirred 2 hr. at −78° C. and then the flask was warmed to room temperature were it was stirred overnight. Solvent was removed under reduced pressure and the residue was extracted with 40 ml of hexane and filtered. Solvent was removed under reduced pressure leaving 7.25 g of the silylamine as a yellow liquid. Yield was 96 percent.

$^1$H (C$_6$D$_6$) δ 0.26 (s, 6H), 1.08 (s, br. 1H), 1.18 (s, 9H), 1.94 (s, 3H), 2.94 (s, 2H), 7.11 (t, 1H, $^3J_{H-H}$=7.3 Hz), 7.21 (d, 1H, $^3J_{H-H}$=7.1 Hz), 7.28 (t, 1H, $^3J_{H-H}$=7.4 Hz), 7.55 (d, 1H, $^3J_{H-H}$=7.4 Hz). $^{13}$C{$^1$H}(C$_6$D$_6$) δ 1.14, 12.85, 33.69, 38.64, 49.50, 118.10, 118.81, 123.77, 124.49, 126.34, 141.36, 143.68, 148.54.

Step 2 Preparation of N-(tert-Butyl)-N-(1-(2-methyl-(1H-3-indenyloxy)-1,1-dimethylsilyl)amine, Dilithium Salt

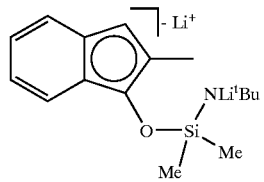

In a drybox 5.00 g (18.15 mmol) of 1-(SiMe2-NH-tBu)-2-Me-indene was combined with 60 ml of hexane. To this solution 27.8 ml (41.75 mmol) of t-BuLi (1.5 M) was added dropwise. Upon complete addition of the t-BuLi, the solution was stirred for 7 h at room temperature. The resulting precipitate was collected via filtration, washed with hexane to give 4.91 g of the dithium salt as a yellow solid. Yield was 94 percent.

Step 3 Preparation of Dichloro(N-(1,1-dimethylethyl)-1,1-dimethyl-1-((1,2,3,3a,7a-η)-2-methyl-1H-inden-1-yloxy) silanaminato(1-)-titanium

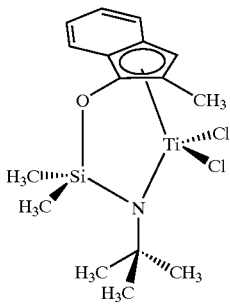

In a drybox 6.335 g (17.10 mmol) of TiCl$_3$(THF)$_3$ was suspended in 80 mL of THF. To this solution 4.910 g (17.10 mmol) of dilithium salt dissolved in 50 mL of THF was added within 5 min. The solution was then stirred for 55 min. After this time 3.09 g of PbCl$_2$ (11.11 mmol) was added and the solution was stirred for 50 min. The THF was then removed under reduced pressure. The residue was extracted with 100 mL of toluene, the solution was filtered, and the toluene was removed under reduced pressure. The residue was then titrated with 60 mL of hexane and the precipitate was collected via filtration on a frit, washed with 60 mL of hexane and dried under vacuum to yield 4.53 g (68 percent yield) of the titanium dichloride.

$^1$H (C$_6$D$_6$) δ 0.40 (s, 3H), 0.44 (s, 3H), 1.42 (s, 9H), 2.09 (s, 3H), 6.16 (s, 1H), 6.86 (t, 1H, $^3J_{H\text{-}H}$=7.6 Hz), 6.98 (t, 1H, $^3J_{H\text{-}H}$=7.5 Hz), 7.14 (d, 1H, $^3J_{H\text{-}H}$=8.6 Hz), 7.43 (d, 1H, $^3J_{H\text{-}H}$=8.5 Hz). $^{13}$C{$^1$H}(C$_6$D$_6$) δ 5.78, 6.78, 14.32, 33.09, 60.69, 106.70, 121.53, 122.19, 125.02, 127.33, 127.40, 142.96.

Polymerizations

A two-liter Parr reactor was charged with 740 g of mixed alkanes solvent and 118 g of 1-octene comonomer. Hydrogen was added as a molecular weight control agent by differential pressure expansion from a 75 mL addition tank at 25 psi (2070 kPa). The reactor was heated to the polymerization temperature of 140° C. and saturated with ethylene at 500 psig (3.4 MPa). Approximately 1.0 μmole of catalyst and cocatalyst (trispentafluorophenyl)borane) as 0.005M solutions in toluene were premixed in the drybox. After the desired premix time, the solution was transferred to a catalyst addition tank and injected into the reactor. The polymerization conditions were maintained for 15 minutes with ethylene on demand. The resulting solution was removed from the reactor, and a hindered phenol antioxidant (Irganox™ 1010 from Ciba Geigy Corporation) was added to the resulting solution. Polymers formed were dried in a vacuum oven set at 120° C. for about 20 hours. Results are contained in Table 1.

TABLE 1

| Run | catalyst | Efficiency (g polymer/mg Ti) |
|---|---|---|
| 1* | A | 977 |
| 2 | B | 45 |
| 3 | C | 11 |

* comparative, not an example of the invention
A N-(1,1-dimethylethyl)-1,1-dimethyl-1-[(1,2,3,4,5-η)-2,3,4,5-tetramethyl-2-4-cyclopentadien-1-yl]silanaminato(2-)-N]dimethyl-titanium
B (N-(1,1-dimethylethyl)-1,1-dimethyl-1-((1,2,3,3a,7a-η)-1H-inden-2-yloxy)silanaminato(2-)dimethyl-titanium (Example 4)
C (N-(1,1-dimethylethyl)-1,1-dimethyl-1-((1,2,3,3a,7a-η)-1H-inden-1-yloxy)silanaminato (1-)dimethyl-titanium (Example 2)

What is claimed is:
1. A metal complex corresponding to the formula:

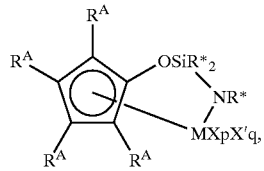

I where M is Ti, which is in the +2, +3 or +4 formal oxidation state;
R$^A$ independently each occurrence is hydrogen, R$^B$ or T'R$^B{}_j$;
j is 1 or 2, and when j is 1, T' is oxygen or sulfur and when j is 2, T' is nitrogen or phosphorus,
R$^B$ independently each occurrence is a group having from 1 to 80 atoms not counting hydrogen, which is hydrocarbyl, hydrocarbylsilyl, halo-substituted hydrocarbyl, hydrocarbyloxy-substituted hydrocarbyl, hydrocarbylamino-substituted hydrocarbyl, or hydrocarbylsilyl-substituted hydrocarbyl, or two R$^B$ groups are joined together forming a divalent ligand group;
R* independently each occurrence is hydrogen, or a member selected from hydrocarbyl, hydrocarbyloxy, silyl, halogenated alkyl, halogenated aryl, and combinations thereof, said R* having up to 20 nonhydrogen atoms;
X is an anionic or dianionic ligand group having up to 60 atoms;
X' independently each occurrence is a Lewis base ligand having up to 20 atoms;
p is a number from 0, 1 or two;
q is zero, 1 or 2.

2. The complex of claim 1, corresponding to the formula:

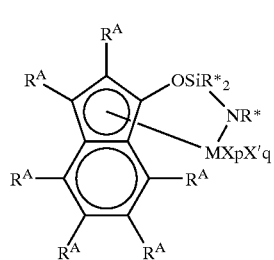

II where R$^A$, R*, M, X, X', and q are as previously defined in claim 1, and
p is 0, 1 or 2.

3. The metal complex of claim 2 wherein:
R$^A$ independently each occurrence is hydrogen, alkyl, aryl, aralkyl, alkoxy, dihydrocarbylamino, or hydrocarbyleneamino, said R$^A$ group having from 1 to 20 nonhydrogen atoms;
X groups are halide, alkyl, cycloalkyl, aryl, aralkyl or cycloalkadienyl groups, said X having from 1 to 20 atoms other than hydrogen;
X' groups are selected from the group consisting of carbon monoxide, trimethylphosphine, triethylphosphine, triphenylphosphine, bis(1,2-dimethylphosphino) ethane, P(OR$^c$)$_3$, wherein R$^c$ is hydrocarbyl, silyl and combinations thereof, ethers, pyridine, bipyridine, tetramethylethylenediamine, triethylamine, olefins, of and conjugated dienes having from 4 to 20 carbon atoms.

4. The metal complex of claim 3 wherein $R^A$ independently each occurrence is hydrogen, or alkyl.

5. A metal complex according to claim 3 corresponding to the formula:

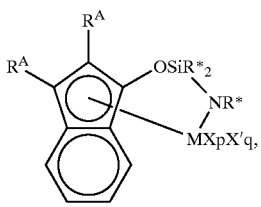

III where, $R^A$, $R^*$, M, X, X', p and q are as previously defined in claim 3.

6. The metal complex of claim 1 corresponding to the formula:

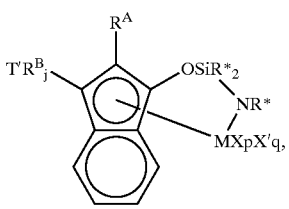

IV where $R^A$, $T'R^B_j$, $R^*$, M, X, X', p and q are as previously defined in claim 1.

7. A catalyst composition for olefin polymerization comprising:

(A) a catalyst component comprising a metal complex of claim 1; and (B) a cocatalyst component comprising an activating cocatalyst wherein the molar ratio of (A) to (B) is from 1:10,000 to 100:1; or optionally catalyst component (A) is activated by use of an activating technique.

8. A process for polymerizing olefins comprising contacting one or more $C_{2-20}$ α-olefins under polymerization conditions with a catalyst composition of claim 7.

9. A metal complex according to claim 1 selected from the group consisting of:

dichloro(N-(1,1-dimethylethyl)-1,1-dimethyl-1-((1,2,3,3a,7a-η)-1H-inden-1-yloxy)silanaminato(1-)-titanium, (N-(1,1-dimethylethyl)-1,1-dimethyl-1-((1,2,3,3a,7a-η))-1H-inden-1-yloxy)silanaminato(1-)dimethyl-titanium, dichloro(N-(1,1-dimethylethyl)-1,1-dimethyl-1-((1,2,3,3a,7a-η)-1H-inden-2-yloxy)silanaminato(2-)-titanium, (N-(1,1-dimethylethyl)-1,1-dimethyl-1-((1,2,3,3a,7a-η)-1H-inden-2-yloxy)silanaminato(2-)-dimethyl-titanium, and dichloro(N-(1,1-dimethylethyl)-1,1-dimethyl-1-((1,2,3,3a,7a-η)-2-methyl-1H-inden-1-yloxy)silanaminato (1-)-titanium.

10. A catalyst composition for olefin polymerization comprising:

(A) a catalyst component comprising a metal complex of claim 2; and (B) a cocatalyst component comprising an activating cocatalyst wherein the molar ratio of (A) to (B) is from 1:10,000 to 100:1; or optionally catalyst component (A) is activated by use of an activating technique.

11. A catalyst composition for olefin polymerization comprising:

(A) a catalyst component comprising a metal complex of claim 3; and (B) a cocatalyst component comprising an activating cocatalyst wherein the molar ratio of (A) to (B) is from 1:10,000 to 100:1; or optionally catalyst component (A) is activated by use of an activating technique.

12. A catalyst composition for olefin polymerization comprising:

(A) a catalyst component comprising a metal complex of claim 4; and (B) a cocatalyst component comprising an activating cocatalyst wherein the molar ratio of (A) to (B) is from 1:10,000 to 100:1; or optionally catalyst component (A) is activated by use of an activating technique.

13. A catalyst composition for olefin polymerization comprising:

(A) a catalyst component comprising a metal complex of claim 5; and (B) a cocatalyst component comprising an activating cocatalyst wherein the molar ratio of (A) to (B) is from 1:10,000 to 100:1; or optionally catalyst component (A) is activated by use of an activating technique.

14. A catalyst composition for olefin polymerization comprising:

(A) a catalyst component comprising a metal complex of claim 6; and (B) a cocatalyst component comprising an activating cocatalyst wherein the molar ratio of (A) to (B) is from 1:10,000 to 100:1; or optionally catalyst component (A) is activated by use of an activating technique.

15. A catalyst composition for olefin polymerization comprising:

(A) a catalyst component comprising a metal complex of claim 9; and (B) a cocatalyst component comprising an activating cocatalyst wherein the molar ratio of (A) to (B) is from 1:10,000 to 100:1; or optionally catalyst component (A) is activated by use of an activating technique.

16. A process for polymerizing olefins comprising contacting one or more $C_{2-20}$ α-olefins under polymerization conditions with a catalyst composition of claim 10.

17. A process for polymerizing olefins comprising contacting one or more $C_{2-20}$ α-olefins under polymerization conditions with a catalyst composition of claim 11.

18. A process for polymerizing olefins comprising contacting one or more $C_{2-20}$ α-olefins under polymerization conditions with a catalyst composition of claim 13.

19. A process for polymerizing olefins comprising contacting one or more $C_{2-20}$ α-olefins under polymerization conditions with a catalyst composition of claim 14.

20. A process for polymerizing olefins comprising contacting one or more $C_{2-20}$ α-olefins under polymerization conditions with a catalyst composition of claim 15.

* * * * *